Feb. 25, 1969 C. F. CHAPLIN Plant Pat. 2,869
DIEFFENBACHIA PLANT
Filed Aug. 14, 1967
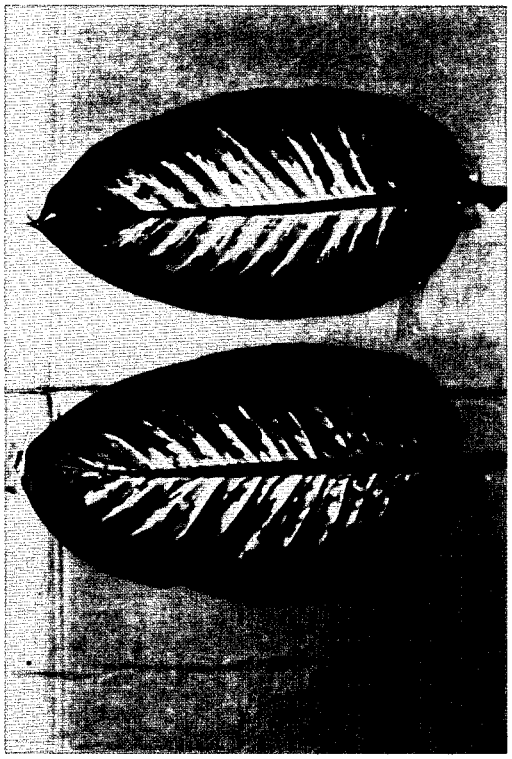
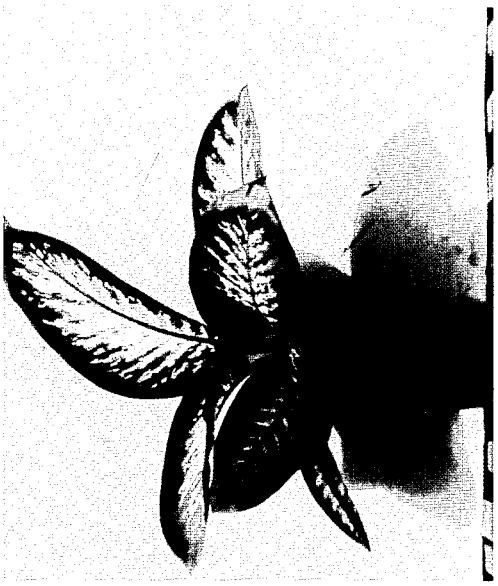
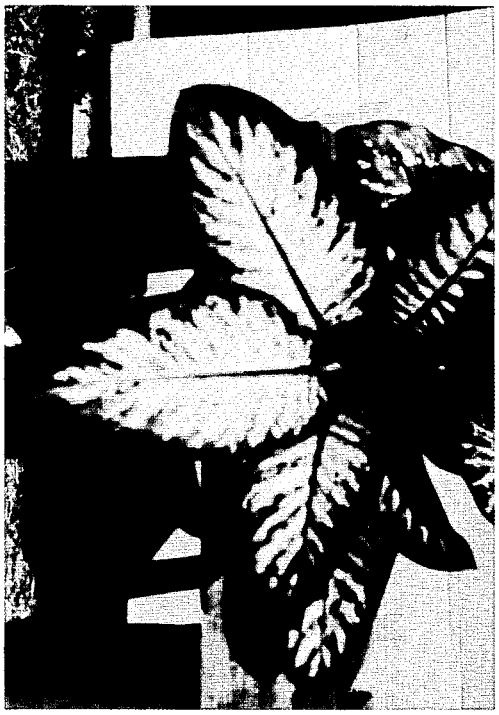
Inventor.
Charles F. Chaplin
By: Robb & Robb
Attorneys.

United States Patent Office

Plant Pat. 2,869
Patented Feb. 25, 1969

2,869
DIEFFENBACHIA PLANT

Charles F. Chaplin, Rte. 1, Box 355,
Fort Lauderdale, Fla. 33314

Filed Aug. 14, 1967, Ser. No. 660,533
U.S. Cl. Plt.—88 1 Claim
Int. Cl. A01h 5/12

The present invention relates to a new and distinct variety of Dieffenbachia plant which was discovered by me in a shade house on my nursery property located at Davie, Fla., as a sport of the unpatented *Dieffenbachia amoena.*

At the time of my discovery aforesaid, I was commercially growing a block of *Dieffenbachia amoena* in a shade house on my nursery property, and in the course of these growing operations, my attention was attracted to one particular plant in this block which bore some variegated leaves quite different in appearance from the other leaves on this plant and different from those of all other plants in this block, as well as strikingly different from the leaves of all other Dieffenbachia varieties previously known to me. Upon close inspection of this particular plant, I found that it had sported from a stem near the ground, and I accordingly took immediate steps to preserve the sport and keep it under close observation. Shortly thereafter, I took tip and cane cuttings from the sport to propagate the same, as performed by me in my nursery aforementioned.

Continued observations and tests of the sport and the progeny thereof derived from the cuttings aforesaid, have convinced me that it represents a new and improved variety which is distinctly different from the parent variety, as well as from all other Dieffenbachia varieties of which I am aware, as evidenced from the following unique combination of characteristics which are outstanding therein:

(1) A general similarity to the parent variety, *Dieffenbachia amoena*, but having a more compact plant habit, slightly shorter leaves, and shorter petioles and internodes which give the plant a more compact form; and (2) A distinctive and highly attractive, variegated coloration of the leaves ranging from white to cream over a large, usually solid, irregular, central area ending outward from the midrib sometimes to nearly the marginal edge of the leaf, which sharply contrasts with dark green edge of the leaf which shades into light green around the bright central area.

In comparison with its parent variety, *D. amoena,* the leaves of the new variety give the impression of having a striking, livelier, and large central field of a solid white to cream or ivory color which appears like a "painted" center that sharply contrasts with the green colored marginal areas of the leaves, as distinguished from typical light colored streaks, narrow stripes or bands which extend outwardly from the midrib in substantially parallel relation to each other in the case of the parent variety. On the average, the light colored central field occupies from about 30% to 60% of the leaf surface area in the case of the new variety, while the stripes or bands represent only about 5% to 20% of the leaf area in the parent variety.

The accompanying drawing shows a typical specimen plant of my new variety, as well as the upper and under surfaces of typical specimen leaves on an enlarged scale, as depicted in color as nearly true as it is reasonably possible to make the same in a color illustration of this character.

The following is a detailed description of my new Dieffenbachia variety, as based on observations of specimen plants grown in my nursery at Davie, Fla., with color terminology in accordance with Wilson's Horticultural Colour Chart, published in collaboration with the Royal Horticultural Society, except where general color terms of ordinary dictionary significance are obvious:

Parentage: Sport of *Dieffenbachia amoena.*

Propagation: Holds its distinguishing characteristics through succeeding propagations by tip and cane cuttings.

*Plant*

Form: Upright; compact.

Growth: Vigorous.

Blooming habit: Has never bloomed.

Foliage:

*Size.*—Ranges from 3 inches to 4 inches long in young stage to 20 inches to 24 inches long in adult stage, with average length about 13 inches when mature, and average width about 7½ inches.

*Quantity.*—Normal.

*Color.*—

New foliage: upper side—a high degree of glossy cream-white central area with pronounced dark green beginning at midrib, with remainder of leaf ranging from darker than Scheele's Green, Plate 860, page 175, to lighter than Scheele's Green, Plate 860/3, page 175, with the cream-white area diminishing near vein ends and surrounded by dark glossy green margins extended inward between veins and terminating in mottled dark green, becoming somewhat transparent adjacent to the light colored field; sometimes the light colored field varies and does not run together as a solid color on some of the lower leaves; underside—substantially the same as the upper side. Old foliage: upper side—approximately the same as in the new foliage, except that the lighter green colors of the new foliage tend to become darker and heavier in appearance with slightly less white and more cream in the central field; under side—about the same as the upper side.

*Shape.*—Large ovate, with cordate base.

*Texture.*—Smooth on both upper and under sides.

*Margin.*—Slightly undulate; revolute.

*Petiole.*—About 8 inches long.

*Internodes.*—Between about ¾ inch and 1 inch in a plant ranging from about 2 feet to 3 feet tall.

Canes: About 1¾ inch to 2 inches in diameter when from 2 feet to 3 feet tall.

Disease resistance: Comparable to that of *Dieffenbachia amoena,* as determined by comparison with that variety grown under the same cultural conditions at Davie, Fla.

*Flowers*

Flower: None produced.

*General observations*

Hardiness: Survives at temperature as low as 32° F., but loses leaves below 50° F.; grows well in Florida over temperature ranging from 50° F. to 100° F.

Outstanding features: The new variety seems to have all the virtues of its parent variety which is one of the most durable of all Dieffenbachia varieties, plus a spectacularly higher color, both in the amount of white color and in color contrast, as well as a more compact and more attractively shaped plant habit.

I claim:

1. A new and distinct variety of Dieffenbachia plant, substantially as herein shown and described, characterized particularly as to novelty by the unique combination of a general similarity to the parent variety, *Dieffenbachia amoena,* but having a more compact plant habit, slightly shorter leaves, and shorter petioles and internodes which give the plant a more compact form, and a distinctive and highly attractive, variegated coloration of the leaves ranging from white to cream over a large, solid, irregular, central area ending outward from the midrib sometimes to nearly the marginal edge of the leaf, which sharply contrasts with dark green edge of the leaf which shades into light green around the bright central area.

No references cited.

ROBERT E. BAGWILL, *Primary Examiner.*